United States Patent [19]

Messineo et al.

[11] 4,396,600
[45] Aug. 2, 1983

[54] ADULT SCHISTOSOME WORM-DERIVED ANTIGENIC SUBSTANCE AND METHOD OF OBTAINING SAME

[75] Inventors: Luigi Messineo, Broadview Heights, Ohio; Mauro Scarpin, Rio de Janeiro, Brazil

[73] Assignees: Gus Gallucci; Mike Gallucci, both of Akron, Ohio; Michael Gallucci, Jr., Broadview Heights, Ohio; Don Lower, Leesburg, Va. ; part interest to each

[21] Appl. No.: 217,575

[22] Filed: Dec. 18, 1980

[51] Int. Cl.$^3$ .............................................. A61K 39/002
[52] U.S. Cl. ................................ 424/88; 260/112 R; 424/85; 424/93; 424/177; 436/515
[58] Field of Search ...................... 424/85, 88, 93, 177; 260/112 R

[56] References Cited

U.S. PATENT DOCUMENTS

4,150,107 4/1979 Enders ............................ 424/88 X
4,158,049 6/1979 Pelley ............................. 424/88 X

OTHER PUBLICATIONS

Madison, J. Parasit, vol. 64, No. 6, 1978, pp. 986–993.
Pelley, Am. J. Trop. Med. Hyg., vol. 26, 1977, pp. 104–112.
Boctor, J. Immunology, vol. 122, No. 1., Jan. 1979, pp. 39–43.
Carter, J. Immunology, vol. 122, No. 6, Jun. 1979, pp. 2204–2209.
Harrison, J. Immunology, vol. 122, No. 6, Jun. 1979, pp. 2210–2217.
Sadun, Military Med., vol. 124, 1959, pp. 428–436.

*Primary Examiner*—Anna P. Fagelson
*Attorney, Agent, or Firm*—Sherman & Shalloway

[57] ABSTRACT

An extract of adult Schistosome mansoni worms, obtained by incubation in 0.15 M sodium chloride-sodium phosphate buffer (pH 6.8), contains protein, carbohydrates, and nucleic acid and/or by-products of the latter component and resolves into four major fractions by gel chromatography in G-100 and G-200 Sephadex columns. Immunodiffusion tests with rabbit anti-total extract serum reveal three precipitation lines corresponding to fractions I and II, and one with III or IV. Rabbits immunized with this total extract are found to be totally or partially (at least 77%) resistant to a challenge infection. The saline extract antigenic material is an effective vaccine for the treatment and immunization of schistosomiasis and other schistosome infections.

23 Claims, 9 Drawing Figures

ADULT SCHISTOSOME WORM-DERIVED ANTIGENIC SUBSTANCE AND METHOD OF OBTAINING SAME

BACKGROUND OF THE INVENTION

This invention relates to the isolation of antigenic material from Schistosomes useful in the treatment of schistosomiasis in animals. More particularly, this invention relates to the extraction and isolation of antigenic material from living, adult schistosomes and the treatment of animals with the extracted antigenic material to treat and/or immunize against schistosome infection.

As used in this specification, the word "schistosome" will be used as a general term which will be understood to refer to the Trematode parasitic worms *Schistosoma mansoni*, *Schistosoma japonicum*, and *Schistosoma hematobium*.

Schistosomes are parasitic worms existing in many areas of the world, principally in Africa, Asia, and South America which, in their adult stage, are capable of residing in various organs of animals, particularly mammals, such as cattle and humans, primarily in the mesenteric and pelvic veins. The existance of schistosomes is particularly prevalent in tropical and underdeveloped countries of the world. Schistosoma have been characterized as the major helminth pathogen of man.

Schistosome eggs are produced by adult pairs of schistosomes located within the body of a host. The eggs are eliminated from the host's body, usually in the feces or urine. Schistosome eggs hatch into miracidia which develop into a larval stage in the body of any of several mollusks, generally of the snail type, as is well known by those skilled in the art. The larvae (cercaria) are then released to and live in open water systems, such as ponds, rivers, streams, etc. until they are able to infest an animal host.

The cercaria usually enter a mammalian host through the skin, generally in the extremities, such as a foot pad. The cercaria bore very quickly into the skin and travel through the lymphatic system of the host. In the lungs of the host, the cercaria develop to a second larval stage and move from the lungs to their final residence in some portion of the host's body. The second stage larval development proceeds to the adult stage, usually in an organ of the body such as the liver, vena porta or other similar body location. The development of the larvae from the time of entry through the skin to the adult stage takes place in a period of about four to about six weeks. The adult worms form mating pairs and begin immediately to produce eggs which extend the life cycle.

There have been several attempts to isolate extracts having antigenic-immune reaction activity from the various stages of the schistosome life cycle, especially from schistosome eggs (soluble egg antigen-SEA), as well as whole and ground adult worms.

According to one such procedure, live worms are perfused from an infected host, e.g., mice, rat, or rabbit, and are then injected into a test animal. Only minor reductions in worm burden upon challenge with injected cercaria or adult worms is provided by this procedure.

Other studies with antigens derived from adult worms by several different procedures are reported by Shirley E. Maddison, et al., "Studies of Putative Adult Worm-Derived Vaccines and Adjuvants for Protection Against Schistosoma Mansoni Infection in Mice", *Journal of Parasitology*, Vol. 64, No. 6, pp 986–993 (1978). In one procedure, freshly ground worms (FCW) are prepared by perfusing adult worms from mice with citrate saline at 4° C., collecting the worms in a small amount of Hank's Balanced Salt Solution (HBSS), homogenizing at 4° C. in a tissue grinder, and using the homogenate for injection. In another approach, whole worm extract is prepared from freshly collected adult worms by homogenizing the worms with a small amount of phosphate-buffered saline (PBS) in a tissue grinder. The suspension is clarified by centrifugation and the supernatant fluid is dialyzed against PBS.

With any of these procedures, when test animals which have been injected with the putative worm antigen are challenge-infected with a known number of schistosome cercaria, the percent reduction in the worm burden of the test animals, compared to similar controls, and based on the number of cercaria in the initial infection, ranged from 0–30%.

Greater reductions in the worm burden (up to 52%) are shown by Maddison et al. when the putative antigens from a modified procedure are combined with an injection of a bacteria such as *Corynebacterium Parvum*.

In the modified procedure, the putative antigen is extracted from adult worms with 0.5 M KCl/1.0 M NaCl. The adult worms are collected at 4° C. and are homogenized in a tissue grinder with a small amount of HBSS in which the worms are collected. Within 30 minutes, the worm homogenate is frozen in dry ice and alcohol at below −100° C. Approximately 5000 of the homogenized worms are extracted with 50 ml of cold extraction medium (0.5 M KCl, 1.0 M NaCl, 2 mM EDTA, 1 mM DL-cysteine HCl in Tris HCl 0.05 M; pH=3.0). The mixture is stirred for 15 minutes at 4° C. and the extract is clarified by centrifugation. The supernatant is held at 4° C. and the solid pellet is re-extracted two times and all the supernatants are pooled and then precipitated by addition of 30% w/v of ammonium sulfate. The suspension is centrifuged (12,000 g for 30 minutes) and the precipitate is redissolved and exhaustively dialyzed against 0.1 M NaCl, 2 mM EDTA, 1 mM DL-cysteine HCl, in Tris HCl 0.05 M; pH=7.6).

In these tests, however, no parallel testing was performed with only the putative antigen without the additional bacteria injections. However, a decreasing concentration of bacteria in the injections (in conjunction with the same amount of putative antigen) shows a decreasing percent reduction in the worm burden. From this, it can be deduced that the primary material responsible for the reduction in the worm burden is the bacteria rather than the putative antigen.

Soluble egg antigen (SEA) from schistosomes are prepared by the techniques shown in the following exemplary publications (as well as references cited therein): Ronald P. Pelley, "Purification of Schistosoma Mansoni Egg Antigens: Theory and Practice," *Am. J. Trop. Med. Hyg.* 26:104–112 (1977); Fouad N. Boctor, et al., "Isolation of a Polysaccharide Antigen From Schistosoma Mansoni Eggs," *J. Immunology*, Vol. 122, No. 1, pp 39–43 (January 1979); Clint E. Carter and Daniel G. Colley, "Partial Purification and Characterization of Schistosoma Mansoni Soluble Egg Antigen With Con A-Sepharose Chromatography," *J. Immunology*, Vol. 122, No. 6, pp 2204–2209 (June 1979); D. Janiece Harrison et al. "Immunoaffinity Purification of Schistosoma Mansoni Soluble Egg Antigens," *J. Immunology*, Vol. 122, No. 6, pp 2210–2217 (June 1979).

For example, according to the technique of Pelley, about 4,000,000 eggs of *Schistosoma mansoni* collected from 50 mice are ground in a tissue grinder in 5 ml of 0.5 M NaCl-Con A (concanavilin A) buffer. The suspension is subjected to ultracentrifugation (100,000 g for 2 hours). The supernatant is desalted on Sephadex G-25 (2×29 cm column, 0.5 M NaCl—Con A buffer). The desalted supernatant is then subjected to affinity chromatography on Con A Sepharose (1.6×21 cm column, 0.5 M NaCl—Con A buffer) eluted with methyl alpha mannose. After concentration of the eluate overnight and dialysis against DEAE buffer, the purified antigen (about 0.2 mg) is obtained by ion exchange chromatography on DEAE cellulose.

The use of blood serum extracted from infected hosts has also met with some success. Serum is collected and concentrated before injection into a test animal. Upon challenge infection by a counted number of cercaria, serum-immunized hosts have shown significant reductions in the worm burden when compared to non-immunized controls.

Nevertheless, still further improvements in the effectiveness in the treatment of and immunization against schistosomiasis and other schistosome induced diseases are required.

Accordingly, it is an object of this invention to provide antigenic material derived from live adult schistosomes which stimulate an immune reaction, thereby protecting an animal host against infection with schistosomes.

Moreover, it is another object of this invention to provide a method of immunizing an animal host against schistosome infection including a method for obtaining antigenic material from live adult schistosomes.

It is a further object of the invention to provide the antigenic material in such pure or nearly pure form as to permit its use as a vaccine in mammals, including humans.

SUMMARY OF THE INVENTION

These and other objects are provided by a live schistosome worm-derived antigen which is extracted from live adult schistosomes by a process which includes the steps of collecting fresh, living adult schistosomes from an infected host animal, prerinsing the worms with a minimal amount of washing solution sufficient to remove blood and other non-worm solids, and extracting the antigenic substance by contacting the worms with a saline extraction solution for at least 30 minutes. After removal of the worms from the extracting solution, the extracting solution is passed through separating means, such as a centrifuge, a filter capable of retaining solution components having a molecular weight greater than about 50,000 or a molecular sieve which passes through high molecular weight components. Combinations of two or more of these separating means, in any sequence, can also be used. The recovered material, having a molecular weight greater than at least 50,000, contains the isolated antigenic substance and, as necessary, collections from several batches of worms may be combined. Upon injection of the recovered material into an animal, the antigen contained therein stimulates an immune reaction activity which results in almost total immunization of the animal against schistosome infection.

Moreover, in accordance with the invention, the schistosomes, which have been separated from the extracting solution in the above process, may be homogenized in additional saline solution. The homogenized schistosomes are then centrifuged and the supernatant liquid from the step of centrifuging may be combined with the original collecting solution prior to passing the solution through the separation means. This procedure results in a somewhat greater amount of recovered antigenic material.

In a preferred embodiment of the invention, the saline solution used in the above described process is buffered at a pH of about 6.8 using a phosphate buffer.

In an alternative embodiment of the invention, after the live perfused worms are minimally rinsed, the worms are homogenized in a tissue grinding apparatus using a small amount of the saline extraction solvent to allow the extraction of the antigenic material. If desired the homogenizing extraction step can be repeated one or more times and the supernatants combined with each other. Sufficient quantities of antigenic material are recovered from the macerated worms after 30 minutes contact time with the extraction solvent. The supernatant possesses the ability to stimulate the immune reaction, but preferably is then subjected to further purification as described below to remove non-antigenic determinant material.

In an especially preferred modification of the invention, applicable to both embodiments described above, the live schistosome worm-derived antigen is further purified by employing as the separator means a gel chromatography partition column, such as Sephadex G-100 or Sephadex G-200, and isolating the first and second fractions eluted from the columns, wherein the first and second fractions are highly purified and include substantially all of the antigenic material.

The further purification of the antigenic material by partition chromatography can follow the separation filtration, sieving, or centrifugation steps described above in the first embodiment or it can be applied to the supernatant from the centrifuging separation of the alternative embodiment.

In yet another aspect of the invention, antigenic material isolated by the above procedure is used in a method of immunizing an animal host against infection by schistosomes. An effective amount of the antigenic substance obtained by either of the above procedures is injected in the animal to stimulate an immune response.

DETAILED DESCRIPTION OF THE INVENTION

The saline extracts from live adult worms, according to this invention, which have been shown to provide protection against infection by schistosomes, have been derived from the species *Schistosoma mansoni*. However, similar results are expected for the species *Schistosoma japonicum* and *Schistosoma hematobium*.

Although not wishing to be bound by any particular theory, it is believed that the live worm saline extract of this invention, when injected into a host animal, induces the host to form complementary antibodies which are effective in attacking the schistosome in its larval stage as soon as the cercaria enter the host and before the schistosoma life cycle can proceed to the adult stage. This property is believed to result from the fact that as the schistosome parasites pass in their developmental stage from the larval stage to the adult stage, the ectoderm of the larva is transformed into the endoderm of the adult worm. It is hypothesized by the inventors that the saline extraction extracts endodermic material from the adult worm which functions as an antigenic material which protects the host mammal.

It is, therefore, a critical feature of the present invention that the perfused adult worms are only minimally washed in the prerinsing step. Thus, previous workers that have attempted to extract antigenic substances from live adult worms have thoroughly rinsed the worms prior to performing the extraction. Such thorough washing results in discarding important antigenic substances from the endoderm, such as one or more of proteins, carbohydrates, nucleotides, nucleic acids, and byproducts of these substances.

In addition, cytotoxic tests have demonstrated that the extract is directly toxic to schistosomulas. Therefore, the live worm saline extract is not only effective in providing immunization against infection by schistosomes, but it is also effective in treating an infected host.

Adult worms, from which the antigenic materials are extracted, are readily available from a number of sources. As an example, the adult worms can be maintained in sufficiently large quantities for laboratory use in Swiss mice, which can be infested with cercaria from snails, e.g., *Biomphalaria glabrata*. Worms can also be maintained in other appropriate animal cultures, e.g., hamsters, guinea pigs, monkeys, cows, etc., as is well known in the art.

The adult worms are collected from the host at the peak of maturity, generally from six to eight weeks after infection. Collection of the worms is accomplished by sacrificing the host and perfusing the infected organs, e.g., liver, mesenteric vein, etc., with a saline solution, preferably isotonic saline of 0.15 M NaCl. A buffer can be added in an amount sufficient to provide a near neutral to slightly alkaline pH in the range of from about 6.8 to about 7.4, preferably from about 6.8 to about 7.2. The preferred buffer is sodium phosphate, but other alkali metal or alkaline earth metal phosphates can also be used. The preferred perfusion fluid is a sodium phosphate buffered 0.15 M NaCl solution, pH 6.8 (PBS).

After the perfused worms are collected, they are rinsed briefly, preferably using the same solution as used for the perfusion, especially PBS.

It is essential in this invention that the amount of rinsing solution and time of contact of the worm with the rinsing solution be kept to the minimum, sufficient to wash away blood and non-worm blood solids, but not any significant amount of worm by-products such as proteins, sugars, nucleic acids, nucleotides and related potential antigenic materials.

The total amount of rinsing solution should therefore be within the range of about 5 to about 30 ml per 100 worms, preferably from about 10 to about 20 ml per 100 worms. It is also preferred to use one-half of the total volume of rinsing solution in two rinses, although one or three rinses can also be used. The rinsing can be easily accomplished simply by collecting the perfused worms in an appropriately sized sieve, e.g., a wire net which will not allow the worms to pass through the openings, and slowly pouring or spraying the rinsing solution over the worms. This assures a minimum contact time between the solution and the worms so that only insignificant amounts of antigenic substance will be lost. Since the extraction of the antigenic material with the saline extraction solvent proceeds vary rapidly, this minimum contact time, preferably on the order of a few seconds, is critical.

The washed worms are then stored in a saline extracting solution for a period of time sufficient to extract the antigenic material. Any of the perfusion solution can be used as the saline extracting solution. The pH 6.8 sodium phosphate buffered 0.15 M NaCl (PBS) solution is the preferred extractant.

The amount of saline extracting solution is not particularly critical, but generally is selected so as not to provide too dilute a solution as this makes the recovery of the antigenic material unnecessarily tedious. Generally, amounts in the range of from about 1.0 ml to about 20 ml per gram of worms, preferably from about 5 ml to about 10 ml per gram of worms, are satisfactory. It is also possible to use lesser quantities of extracting solution, e.g., about 1 to 4 ml, and reextract one or more times. Additional recovery of any non-extracted antigenic material can be achieved by homogenating the worm bodies in the saline extracting solution material.

The freshly collected, washed worms are extracted in the saline extraction solvent for a period of at least 30 minutes, preferably from about 30 minutes to about 1 to 2 hours, when allowing the extraction to proceed at ambient temperature conditions, e.g., 15° C. to 35° C. The extraction can also proceed rapidly at cold temperatures, e.g., about 0° C.–10° C. Thus, the extraction can occur by placing the saline extraction solution with the worms under refrigeration, for example, at about 4° C. Under these colder conditions, there is no degradation of the antigenic material for extended periods of time up to several weeks to months, or even longer.

Still further, it is possible to freeze the worm/extraction solvent mixture at temperatures of about −10° C. or lower and to retain the suspension in this frozen state almost indefinitely without degradation of the activity of the antigenic material. If the freezing is accomplished passively, as by placing the worm/saline extraction solvent mixture in a refrigerator-freezer, the extraction of the antigenic material will proceed during the normal freezing time of about 30 minutes or more and again during thawing. If the worm/saline extraction solvent is rapidly frozen in less than 30 minutes, sufficient extraction will not take place until the worm/solvent mixture is thawed.

Although the experience of the inventors is that the worms can be left in the saline extraction solvent at room temperature for many hours, and even one or two days, without chemical reaction or enzymatic degradation occurring, it is nevertheless preferred to avoid storing the worms in the saline extraction solvent at room temperature for periods greatly in excess of a few hours. Moreover, after extraction for one to two hours, there is not expected to be any significant increase in yield of antigenic material, taking into account the probability of extraction solvent coming into contact with all of the organs and membranes of the worm. However, if desired, the worms can be reextracted with additional saline extraction solvent.

In addition to the material obtained directly from the extraction with the saline extractant, it is also possible to extract some additional antigenic material from the worms themselves following their removal from the extraction solvent. To accomplish this, the worms are suspended in additional saline extraction solvent, preferably PBS, and homogenized such as in a tissue grinder, e.g., a Tenbrock tissue grinder. The suspension of homogenized worms and PBS is then centrifuged (10,000 rpm is convenient) to produce a worm solids pellet and supernatant fluid. The supernatant fluid may be combined directly with the live worm-derived saline extraction solution or after dialysis against PBS, as shown by Maddison et al.

It will be understood that this is only a preferred method of increasing the amount of antigen extract recovered. The vast majority of the antigenic material is obtained by the passive saline extraction of the freshly obtained or fresh frozen adult worms.

In an alternative embodiment of the extraction procedure, according to the invention, after the minimal rinsing, the collected worms can be homogenized in the saline extraction solvent to extract the antigenic material. Again, the antigenic material is substantially extracted after about 30 minutes, although longer storage times and freeze-thaw cycles as described above can be used. Any conventional tissue grinder homogenizer can be used to macerate the worms, so long as excessive shearing is avoided, since shearing might degrade the high molecular weight antigenic material.

At the conclusion of the extraction period, the suspension of worms and extraction solvent with extracted substances, after thawing, if necessary, is filtered through an appropriate sieve, such as a steel mesh net, at room temperature, to remove the worm bodies. Alternatively, instead of or after filtering the worm bodies can be removed by centrifuging at low or high speeds, e.g., from about 500 rpm to 10,000 rpm, without losing the antiganic material.

The solids-free, liquid solution, i.e., the supernatant from the centrifuge or the filtrate can be used as such, or after appropriate concentration, as the antigenic material of the invention. When it is not intended to use the antigenic material for any extended length of time, the antigenic material containing solids-free, liquid solution should be kept frozen until ready for use. Storage temperatures of about $-10°$ C. to about $-15°$ C., or lower, are satisfactory.

Other means of separation of the suspended finely divided solid matter, such as ultrafiltration or ultracentrifugation, can also be used. In this case, filters with a pore size capable of retaining high molecular weight substances or a molecular sieve, capable of passing high molecular weight substances, can be used.

For example, the antigenic material containing extract (hereinafter sometimes referred to as the "saline extract") can be further purified by passing the extract through a separating means capable of separating substances having molecular weights of 50,000 or more from substances having molecular weights of below 50,000. As will be shown below, the active antigenic material, in the saline extract of the invention, has been found to have a molecular weight of at least 50,000.

The separation means can be an exclusion pore filter which is capable of retaining solution components having a molecular weight of 50,000 or more, preferably 100,000 or more, for example, a Millipore type filter.

While the saline extract before further separation and after further separation (hereinafter sometimes referred to as "separated saline extract") both include the adult worm-derived antigenic material and are both capable of inducing an immune reaction (e.g., antibody production) in test animals, it is usually necessary to subject the saline extract or separated saline extract to still further purification to obtain the antigenic material in sufficiently isolated form to be used as a vaccine for mammals, including particularly humans.

The further purification of the antigenic material is obtained by partition separation means, such as gel chromatography columns which are capable of separating high molecular weight materials from lower molecular weight materials, for example, Sephadex G-100 or Sephadex G-200, which are bead-formed dextran gel molecular sieves, manufactured by Pharmacia Ltd., Uppsala, Sweden. Biorad beads, which are formed from acrylamide resin, and other similar materials, can also be used to form the partition column. With molecular sieve columns, the higher molecular weight materials are the first fractions to be eluted from the column. The phosphate buffered saline solution (PBS) described previously can be used to equilibrate the gel chromatography column and also as the eluant.

Depending on the exclusion limit of the particular molecular sieve, the saline extracted antigenic material of this invention may either be retained on the column or may be eluted with the voids volume. For example, with partition columns prepared with Sephadex G-100 or Sephadex G-200, having exclusion limits of about 100,000 and about 200,000–400,000, respectively, it has been found that the antigenic material is eluted with the voids volume. With columns prepared with Agarose molecular sieves, having an exclusion limit of about 1,000,000, the antigenic material is retained on the column. In all cases, however, the antigenic material of this invention has been found to comprise molecules of high molecular weight in excess of about 50,000, especially above about 100,000, which is eluted in the first and second peaks of the elution profile, as measured by ultraviolet absorption at 274 nm, of the eluant from the partition column.

The physico-chemical characteristics of the saline extract and separated saline extract of the live adult worms have been qualitatively and quantitatively determined by several techniques, including column chromatography, spectrophotometry, molecular filtration and protein and sugar assays, and nucleic acid assay. These tests have shown that the saline extract of live adult worms, before final purification, contains proteins, sugars, and nucleic acid, and nucleic acid by-products.

Generally, recovery of proteins in the separated saline extract ranges from about 10% to about 30% of the weight of the worms after rinsing. After further purification by gel chromatography, the protein content in the first and second fractions containing the antigenic material ranges from about 2% to about 4% of the total worm weight. Furthermore, the separated saline extract has a sugar content corresponding to about 5% to 20% of the total starting worm weight. After purification by gel chromatography, the sugar content in the first peak ranges from about 0.6 to about 1.5% of the total worm weight. No sugar is found in the second peak.

Based on the physical and chemical analyses, and immunological tests, conducted on the purified saline extract, i.e., after separation by gel partition chromatography, it has been concluded that the antigenic determinant of this invention which is contained in the first and second peaks is a protein, believed to be a glycoprotein. In the first peak, chemical analyses also shows the presence of sugar, but no sugars are found in the second peak. Since both the first and second peaks are immunologically active, as determined by immunological tests, particularly by Ouchterlony immunodiffusion tests, and since the antigenic material in the first and second peaks are cross-reactive with each other against rabbit antiserum from the saline extract, it is concluded that the same antigenic determinant is present in the first and second peaks. It is therefore hypothesized that in the first peak the antigenic material is present in the form of a protein-sugar complex while in the second peak, the antigenic material is present as the protein alone, i.e., the protein-sugar complex dissociates.

This conclusion is also consistent with the observation of two or more precipitation lines on the Ouchterlony immunodiffusion plates which could be attributed to the presence of protein-sugar complexes of different molecular weights resulting from dissociation of, for example, one-half sugar molecule, or one or more sugar molecules.

Furthermore, on the basis of detailed sugar analyses, it has been hypothesized that the sugar is mannose. This conclusion is reached after making a total sugar content analysis by general sugar reducing methods then analyses for specific sugars. The specific sugar analyses made it possible to exclude glucose, ribose, and deoxyribose and to limit the sugar to an exose. Tests for galactose failed to find this sugar. While the analyses for mannose are not deemed to be sufficiently accurate to make a positive determination of the presence of this sugar, the inventors have, nevertheless, been able to predict with a high degree of probability that the unidentified sugar is mannose. This is consistent with the exclusion of other sugars and with the reports in the literature which suggest that mannose is present in schistosomes. Furthermore, mannose is known to be present in animal membranes and, therefore, the presence of mannose is consistent with the inventors' hypothesis that the antigenic material is contained in the endoderm of the adult worms.

The antigenic material of the invention can be used as the active ingredient of a vaccine with conventional carriers and adjuvants, if desired, for immunizing mammals, especially cattle, such as cows, sheep, pigs, horses, etc., as well as humans.

Injections of immunologically effective amounts of antigenic material can be injected subcutaneously into the recipient mammal as a single injection or, preferably, with one or more follow-up booster shots to enhance the immunological reaction, as is well known in the art. The follow-up booster shot, or shots, can be administered, for example, at periods of from about 14 days to 35 days, preferably from about 21 days to 28 days, after the initial injection.

Suitable doses of the antigenic material are generally in the range of from about 1 to about 6 micrograms per pound of body weight, this range being effective for all types of mammals.

The invention will now be described by the following illustrative and non-limiting examples.

EXAMPLE 1

This example shows the preparation of a live worm-derived saline (PBS) extract according to the invention.

*Schistosoma mansoni* (LE strain) cercaria are cultured in *Biomphalaria glabrata* and the adult worms are maintained in Swiss mice. Adult worms are obtained by perfusion of the liver and mesenteric vessels with 0.15 M NaCl solution buffered with sodium phosphate at pH 6.8 (PBS). The worms collected in this fashion are held on a steel net and are rinsed briefly by spraying twice with PBS. Adult worm extract is obtained from 1.0 g of fresh worms stored frozen ($-10°$ C.) in 10 ml of PBS for 10 days. The worm/PBS suspension is thawed and filtered with a steel net at room temperature. The filtrate is centrifuged at 10,000 rpm for 60 minutes at 4° C. and the supernatant is then kept frozen at $-10°$ C. until use. This extract will be referred to as separated saline extract (SE). Similar extracts are prepared by storing separately male and female worms for 30 minutes each (M-30 and F 30, respectively and female worms) for 60 minutes (F-60) in PBS solution.

EXAMPLE 2

This example demonstrates the utility of the separated saline extract (SE) extract for immunizing animals against infection by schistosomes.

Four rabbits are injected intradermally (i.e., subcutaneous injections in the footpads) with 0.6 ml of SE (diluted with PBS to about 1 mg protein/ml) emulsified in complete Freund's adjuvant on day 1, and again on day 7, followed by a booster shot of 1 mg of SE antigen extract injected intraperitoneally on day 21. One control rabbit is injected with mouse serum in a similar scheme in order to check contamination by antigens of host origin. Another rabbit is used as an infection control, i.e., no injections are administered. The rabbits are periodically bled for sera collection over a 45-day period after day 21.

After three to four months, the separated saline extract injected rabbit and the control (non-injected) rabbit are each challenge infected with 700±10 *Schistosome mansoni* cercariae by percutaneous abdominal injection.

Sixty days after the challenge injection, each of the rabbits is sacrificed and an autopsy is performed. Adult schistosomes are perfused from the mesenteric and intrahepatic veins and counted. Percent (%) protection is calculated as number of worms found in the immunized rabbit×100/number of worms in the control rabbit. The results are shown in Table 1.

TABLE 1

Schistosoma mansoni worms recovered in rabbits immunized with SE and in control rabbit after infection with 700 ± 10 cercariae.

| Rabbit | Number of Schistosomes Present | % Protection |
|---|---|---|
| Control | 65 | 0.0% |
| 2 | 0 | 100.0% |
| 3 | 3 | 93.4% |
| 4 | 15 | 77.0% |

In summary, two rabbits showed complete immunity to infection by schistosomes. An overall average protection percentage of 92.5% is achieved. This figure represents a significant increase in the protection afforded immunized mammals over other, prior immunization attempts.

EXAMPLE 3

This example demonstrates the cytotoxic effect of the sera from five separate saline extract (SE) immunized rabbits (RAS), one mouse serum immunized rabbit (RAMS) and two control (non-immunized) rabbits.

Schistosomula are prepared in vitro according to the technique described by F. J. Ramalho-Pinto et al., "*Schistosome mansoni:* Refined system for stepwise transformation of cercaria to schistosomule in vitro." Exp. Parasit. 36: 360–372, 1974. Aliquots of 10 ml of intact cercariae (1500/ml) are cooled in an ice bath for 10 minutes, centrifuged at low speed (500 rpm) for 1 minute and the supernatant is decanted. The packed cercariae are suspended in 2 ml of Earle's saline solution containing 0.5% lactalbumin hydrolysate, 0.1% glucose, 200 units of penicillin and 100 mg of streptomycin (referred to as Elac), and agitated for 45 seconds in a Vortex Jr. mixer. The cercariae tails are removed by transferring a 2 ml suspension to a conical centrifuge tube containing 10 ml of Elac. After 10 minutes, the tail-rich supernatant is decanted and the sedimented bodies are resuspended in 10 ml of the solution. This procedure is repeated twice.

The resulting bodies, containing less that 5% of tails, are suspended in Elac and incubated under continuous shaking at 37° C. for 90–120 minutes, at which the cercariae become water-sensitive and are considered to be 2-hour schistosomula (see Ramalho-Pinto, et al., "Factors affecting surface changes in intact cercariae and cercarial bodies of *Schistosome mansoni*." Parisitol. 71: 19–25, 1975.) Cytotoxic assay is carried out according to the technique described by C.A.P. Tavares—"Estudos in vitro sobre o mecanismo de evaquo do *Schistosoma mansoni* à acaco do anti-corro letal." Waster's Thesis, pp 64, Istituto de Ciencias Biológicas—Universida de Federal do Minas Gerais, Belo Horizonte, 1977. The 2-hour schistosomula (50/ml) are incubated at room temperature under sterile conditions with 0.1 ml of heat inactivated (30 minutes, 56° C.) rabbit serum obtained from the five immunized rabbits, the mouse antiserum immunized rabbit and the two control rabbits. After 30 minutes, the 2-hour schistosomula are washed three times with Elac, suspended in 0.5 ml of Elac plus 50% rabbit serum and 0.5 ml of either fresh or heat-inactivated guinea pig serum and incubated overnight at 37° C. in a humid atmosphere of 5% $CO_2$. To determine the number of dead or damaged schistosomula, aliquots of 0.05 ml–0.1 ml are counted in a stereoscopic microscope. The results are expressed as percentage of dead or damaged schistosomula per total schistosomula counted.

The RAS sera presented 91% to 100% cytotoxic activity, while the RAMS sera and control rabbit sera showed no cytotoxic activity. The cytotoxicity against schistosomula "in vitro" presented by the RAS sera is first detected after 10 days from completion of the immunization scheme and remains at the same high level until the animals are sacrificed. The results are shown in Table 2.

EXAMPLE 4

The live worm separated saline extract (SE) from Example 1 is analyzed to determine its physico-chemical make-up.

Protein determinations are made according to the O. H. Lowrey et al. method: "Protein measurement with the Folin Phenol reagent." *Biol. Chem.* 193: 265–275 (1951) and a modification of the buiret method of G. L. Ellman, "The biuret reaction: Changes in the ultraviolet absorption spectra and its application to the determination of peptide bonds." *Analyt. Biochem.* 3: 40–48, 1962, at 300 nm.

SE is found to contain 0.507 mg protein per ml.

The total carbohydrate-sugar content is determined by the method of L. Messineo and J. D'Amrico: "A test for ribose determination without interference from deoxyribose." *Int. J. Biochem.* 3: 351–356, 1972.

Figure 1:
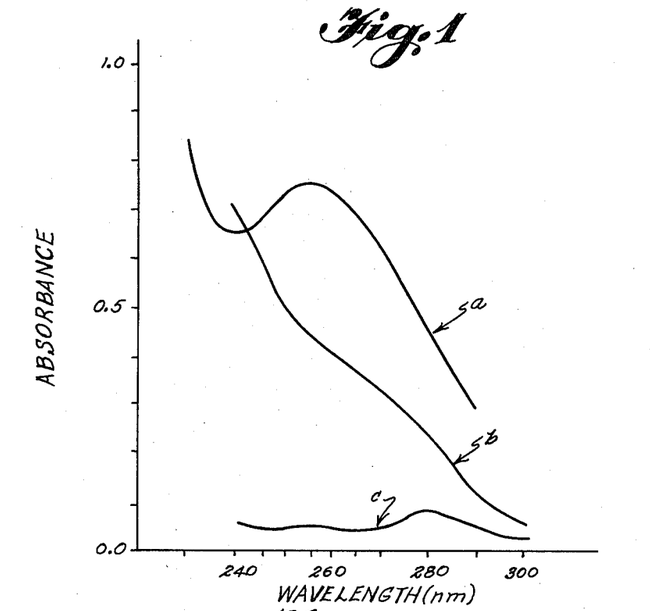
FIG. 1 is a graph showing the ultraviolet absorption spectra of antigenic determinant containing material before gel chromatography and of two different fractions obtained by gel chromatography.

The total amount of aldehexoses and aldopentoses in SE is 0.371 mg/ml. Large amounts of nucleic acid and nucleic acid by-products are also found in SE as determined by spectrophotometry, both before and after deproteinization. Deproteinization is accomplished by mixing an equal volume of SE and trichloroacitic (TCA) (to a final concentration of 0.5 M), heating the mixture at 80° C. for 20 minutes and centrifuging at 5,000 rpm in a clinical centrifuge. The ultraviolet absorption spectra of SE after deproteinization is shown in FIG. 1 (curve (a)).

EXAMPLE 5

This example shows the further resolution of the chemical makeup of the separated saline extract as well as the further purification thereof by gel column chromatography.

TABLE 2

Cytotoxic activity of sera of rabbits immunized with saline extract from adult Schistosome mansoni on schistosomula.

| | Percent of dead *schistosomulae* | | | |
|---|---|---|---|---|
| | dose I | II | III | IV |
| Rabbit Antisera | | | | |
| 1 | 99 | 96 | 100 | 100 |
| 2 | 99 | 97 | 96 | 100 |
| 3 | 95 | 96 | 91 | |
| 4 | 100 | 100 | | |
| 5 | 100 | | | |
| Control | | | | |
| Non immunized rabbit sera | | | | |
| 1 | 0 | 0 | 0 | 0 |
| 2 | 0 | 0 | 0 | 0 |
| Rabbit sera immunized with mice serum | | | | |
| 1 | 0 | 0 | 0 | 0 |

Note:
Dose I > Dose II > Dose III > Dose IV - factor 10.

Fractionation of SE is carried out on Sephadex G-100 (0.9×56 cm) and Sephadex G-200 (1.5×90 cm) columns. The columns are first equilibrated with 0.15 M NaCl buffered to pH 6.8 with sodium phosphate (PBS).

Figure 2:
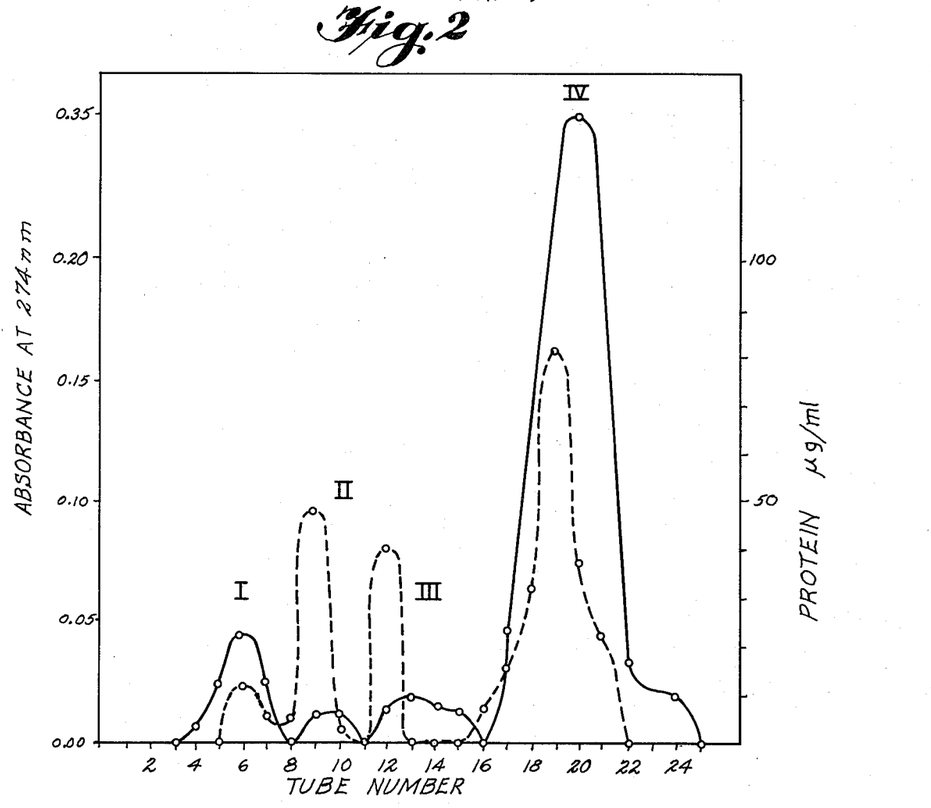
FIG. 2 is a graph showing the elution profile (protein content, UV absorbance) of the antigenic material after separation on a Sephadex G-100 column, according to Example 5.

The SE sample (0.5 ml for the G-100 column and 0.4 ml for the G-200 column) is fed to the column and is eluted with PBS and collected in 1.6 cc aliquots, or 2.5 cc aliquots, respectively. The volume of the extract used in loading the column is always less than 2% of the total column volume. Each aliquot is monitored for its UV absorbance at 274 nm. The results for separation on the Sephadex G-100 column is shown in FIG. 2. Also shown in FIG. 2 is the protein content per ml for each aliquot as measured by the biuret method.

As seen from the elution profile in FIG. 2, four peaks are obtained by the fractionation with SE on the Sephadex G-100 column. Peak I (FI), centered at fraction (tube) 6, is obtained with the void volume. The last three fractions FII, FIII, FIV, centered respectively at fractions 9, 12 and 19/20, are retained by the column. These fractions all give similar partition coefficients (Kav). As an example, the Kav of FII is, in all of the replicated experiments, approximately 0.45. The fact that FI is eluted with the void volume suggests that it is composed of very high molecular weight, i.e., 100,000, and is composed of material having a spherical molecular structure. This conclusion is further supported by the fractionation on Sephadex G-200 wherein the first fraction is also eluted with the void volume. The other fractions are of progressively decreasing molecular weight.

Each aliquot is tested for the presence of protein, sugar, i.e., exoses (aldohexoses and aldopentoses), ribose, deoxyribose, RNA and DNA by the techniques previously described or other standard procedures. Proteins are found in each of fractions I-IV; (FI-3.5 $\mu$g/ml; FII-4.2 $\mu$g/ml; FIII-1.8 $\mu$g/ml; FIV-3.0 $\mu$g/ml); sugar in fractions FI (1.2 $\mu$g/ml), FIII (38.5 $\mu$g/ml), and FIV (36.6 $\mu$g/ml), and nucleic acid and derivatives in FIV.

The ultraviolet absorption spectra of FIV and FI are measured and are shown in FIG. 1, as curves (b) and (c), respectively. Comparison of curve (a) and curve (c) suggests that all nucleic acid material is contained in FIV (absorption peaked at about 240 nm).

Figure 3:
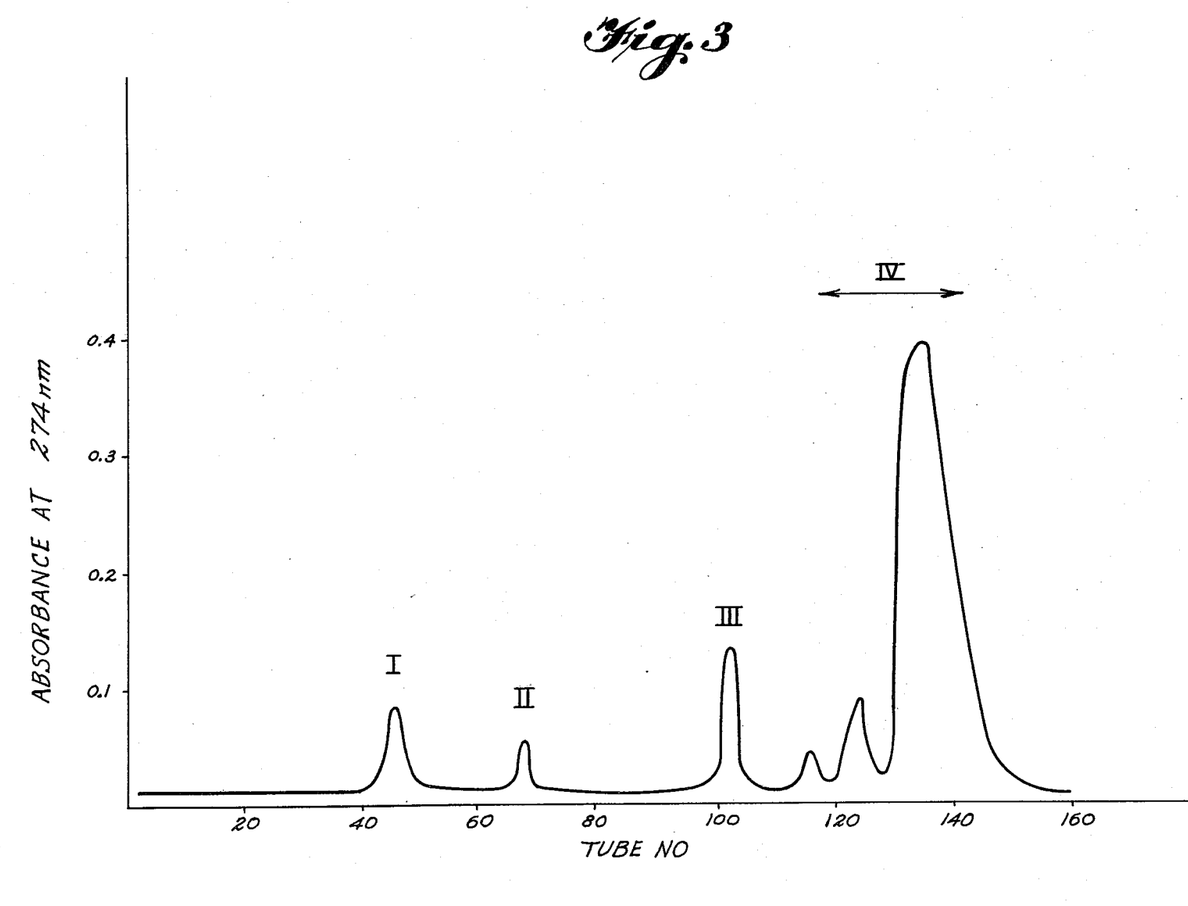
FIG. 3 is a graph showing the elution profile (UV absorbance) of the antigenic material after separation on a Sephadex G-200 column, according to Example 5.

The elution profile with the (1.5×90 cm) Sephadex G-200 column is shown in FIG. 3. As expected, better resolution (larger separation between peaks) is obtained in view of the larger column size and the higher molecular weight exclusion volume of the G-200 column as compared to the G-100 column.

Figure 9:
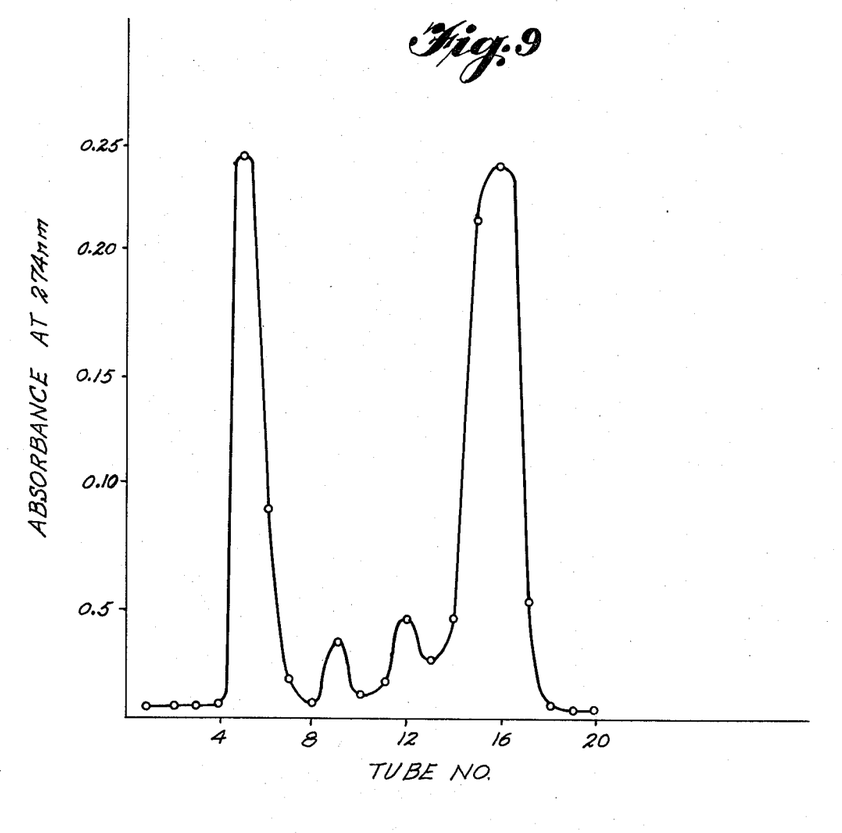
FIG. 9 is a graph showing the elution profile (UV absorbance) of the antigenic material on a different Sephadex G-200 column, according to Example 5.

Similarly, the elution profile of a saline extract of homogenized (ground) adult schistosomes (produced by the alternative embodiment of the invention process) in a 0.9×56 cm Sephadex G-200 column (each aliquot containing 2.6 ml) also shows four well-resolved peaks (see FIG. 9).

Immunological studies (described in Example 6) and the absence of sugars from the second peak (tube Nos. 65-70 in FIG. 3) show that this fraction corresponds to FII (tubes 8-11 in FIG. 2) in the Sephadex G-100 fractionation; while the first peak (tubes 40-50 in FIG. 3) corresponds to FI (tubes 3-7 in FIG. 2).

EXAMPLE 6

Figure 4:
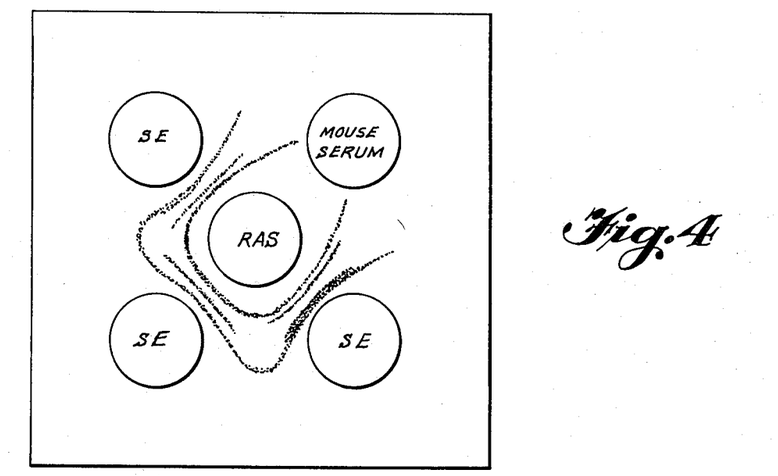
FIG. 4 is an illustration of an Ouchterlony immunodiffusion plate from Example 6.

The immunological activity of the fractions FI, FII, FIII, and FIV, as well as the separated saline extract from Example 1 are determined by the double immunodiffusion technique of O. Ouchterlony, "Diffusion in gel methods for immunological analysis." *Progress in Allergy*, Karger, Basel 5: 1-78, 1958, using the rabbit-anti-SE (RAS) and rabbit-anti-mouse-serum (RAMS) from Example 1, with SE used as antigen. The following technique is used:

Slides are covered with 2 ml of 1% Indubiose in PBS, pH 6.8. Antigen and sera are allowed to diffuse for 24 hours. After diffusion, the slides are washed, dried and stained with 0.25% Coomassie Brilliant Blue made up in a solution of 45 ml of methanol, 45 ml of water and 10 ml of glacial acetic acid, rinsed with the same solution and photographed. The result is shown in FIG. 4.

Two or three precipitation bands, depending on the batch of SE employed, are found in the Ouchterlony immunodiffusion test with RAS. This test confirms that SE contains an antigenic determinant.

An immunodiffusion test with RAMS (rabbit-anti-mouse-serum) against SE does not reveal any precipitation lines (see FIG. 4), thus confirming that no mouse antigenic material determinants are present as contaminants in SE. Accordingly, the antigenic materials in SE are clearly extracted from the live adult schistosome worms.

EXAMPLE 7

Figure 5:
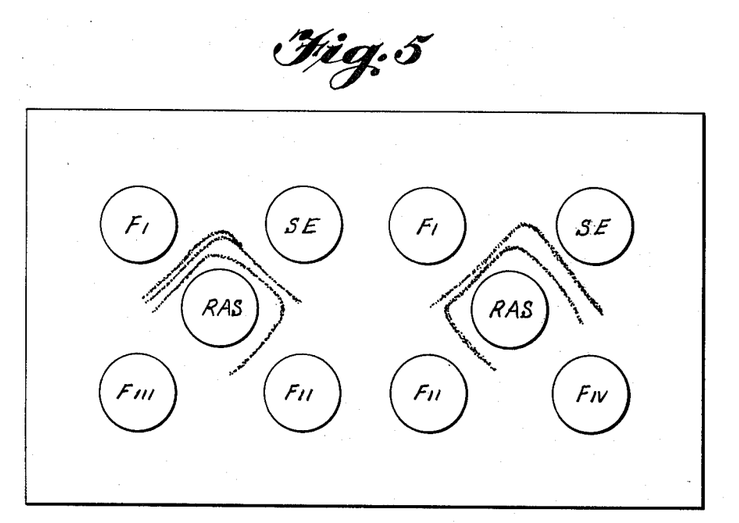
FIG. 5 is an illustration of an Ouchterlony immunodiffusion plate from Example 7.

An Ouchterlony immunodiffusion test is also run with the Sephadex G-100 fractions FI, FII, FIII, and FIV, in which the contents of each tube are concentrated 15-fold. The results are shown in FIG. 5. Only fractions FI and FII give strong precipitation lines. This shows that all of the antigenic substances are contained in the high molecular weight fractions FI and FII, tubes 3-11, of the elution profile shown in FIG. 1. Also shown in FIG. 5 is the precipitation line between the separated saline extract (SE) before purification and the rabbit antiserum (RAS).

FIG. 5 shows the cross-reactivity between FI and FII, as well as between SE and FI and between SE and FII. This indicates that the same antigenic determinant is contained in FI and FII. The multiple precipitation lines for FI suggest that different molecular weight materials are present. These are believed to be due to the reaction or combination of the protein and sugar components in FI.

EXAMPLE 8

Figure 6:
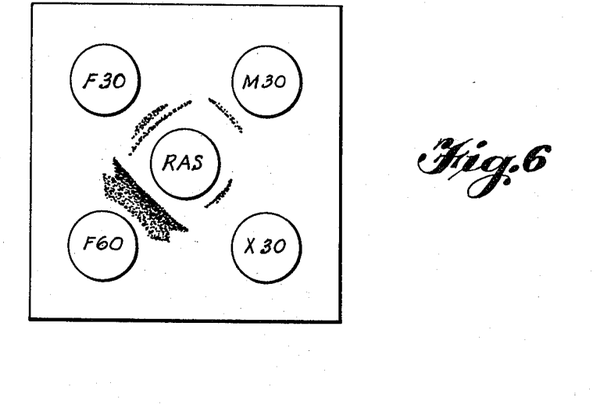
FIG. 6 is an illustration of an Ouchterlony immunodiffusion plate from Example 8.

In still another Ouchterlony diffusion test run with RAS and the male and female worm PBS extracts (F-30 and F-60 and M-30) from example 1 strong precipitation lines are also observed (see FIG. 6). Accordingly both male and female schistosomes contain saline extractable antigenic substances, although the female adults appear to release the antigen faster (as determined by the stronger F30 precepitation line as compared to the M30 precepitation line). This test also shows that it is not necessary to store the live worms in the saline extraction media for long periods of time or to use a freeze-thaw cycle to extract the antigenic substances.

EXAMPLE 9

Figure 7:
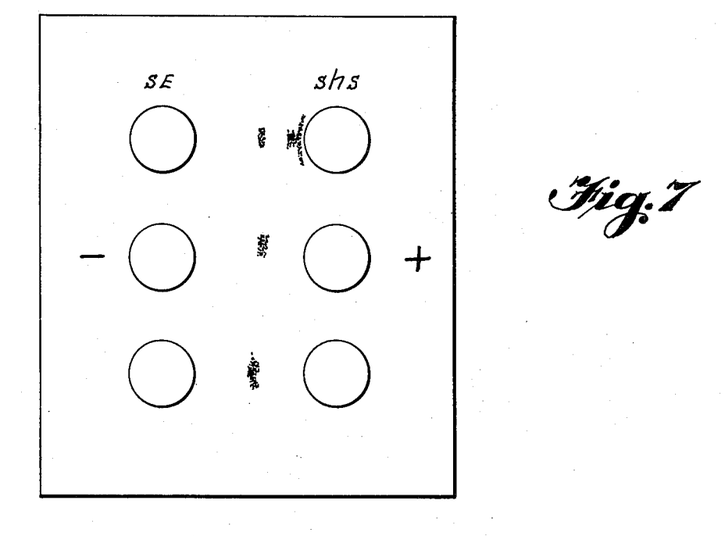
FIG. 7 is an illustration of an Ouchterlony immunodiffusion plate from Example 9.

Evidence of immunological activity in humans is provided by immunoelectroosmophoresis (IEOP) with FI, FII and human sera. Precipitation bands are observed on the IEOP plate shown in FIG. 7. In FIG. 7 the three wells on the left are filled with three different samples of separated saline extract prepared as in example 1. The three wells on the right are filled with sera of human schistosomasis patients. The precipitation bands show that the antigenic determinant extracted from the live adult worms is reactive to the antibodies in the serum of humans that have been infected by schistosomiasis.

EXAMPLE 10

This example shows the results of Ouchterlony immunodiffusion plates between the separated saline extract, SE (from example 1); an homogenized saline extract according to the invention, i.e. minimal pre-rinsing; and the second fractions from separation on a 0.9×56 cm Sephadex G-200 column for the separated saline extract (SE) and the homogenized saline extract. The results are shown in FIG. 8.

Figure 8:
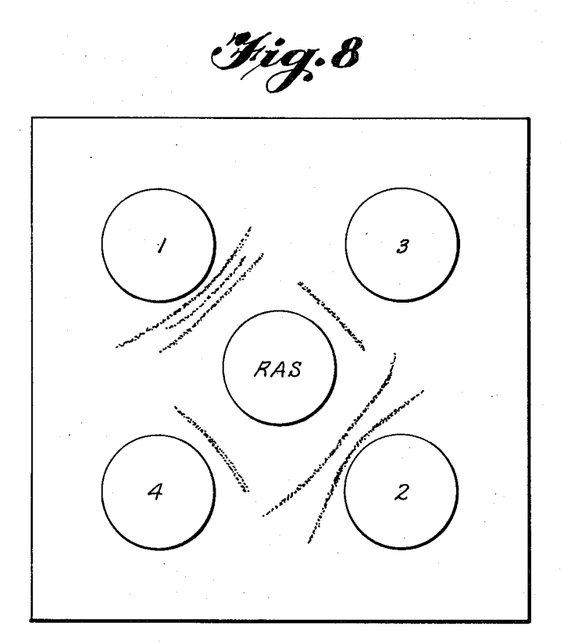
FIG. 8 is an illustration of an immunoelectroosmophoresis plate showing the cross-reactivity of the saline extract of the invention and sera from human schistosomiasis patients from Example 10.

In FIG. 8 the center hole is filled with rabbit antiserum. Hole 1 is filled with separated saline extract, SE, which is obtained by the procedure of example 1. Hole 2 is filled with homogenized saline extract obtained by homogenizing freshly perfused adult worms (which are only minimally washed by two low volume rinses with PBS) in a small volume of PBS and centrifuging the homogenate at 10,000 rpm. The supernatant is collected and used in the immunodiffusion test.

Hole 3 is filled with the fractions constituting the second peak when the separated saline extract, SE, is fractionated on the Sephadex G-200 column. Hole 4 is filled with the fractions constituting the second peak when the homogenized saline extract is subjected to the fractionation on the Sephadex G-200 column.

This test shows the similarity in the active antigenic determinants in each of the extracts and also the greater homogeneity in the homogenized saline extract (two precipitation lines for hole 2 as compared to three precipitation lines for hole 1). However, both fractions are shown to react immunologically with the antiserum to the saline extract in the center hole.

What is claimed is:

1. An antigen-containing extractant capable of developing an immune reaction in mammals to infection by schistosomes comprising a saline extract obtained from live adult schistosomes by the steps of:
    collecting fresh, living adult schistosomes from a host without destroying the schistosomes;
    rinsing the fresh, living adult schistosomes with saline solution to remove only blood and non-worm solids but without removing worm by-products;
    extracting antigenic material from the rinsed adult schistosomes in a saline extracting solution for a period of at least 30 minutes;
    removing the schistosomes from the saline extracting solution; and,
    collecting the remaining solution containing said live worm-derived antigen-containing extractant.

2. The antigen containing extractant of claim 1, wherein the saline solution for said perfusion, said rinsing, and said extracting comprise sodium phosphate buffered sodium chloride.

3. The antigen-containing extractant of claim 2, wherein the perfusion solution and extracting solution comprise 0.15 M NaCl buffered to pH 6.8 by sodium phosphate.

4. The antigen-containing extractant of claim 3, wherein the schistosomes are removed from the saline extracting solution by centrifuging the extracting solution, and the remaining solution comprises the supernatant from said centrifuging step.

5. The antigen-containing extractant as set forth in claim 3, wherein the schistosomes are removed from the saline extraction solution by filtering said extraction solution through an exclusion pore filter having a pore size which retains solution components having molecular weight greater than about 50,000, and the remaining solution comprises the material retained on said filter.

6. The antigen-containing extractant as set forth in claim 3, wherein the schistosomes are removed from the saline extraction solution by filtering said extraction solution through an exclusion pore filter having a pore size which retains solution components having molecular weight greater than about 100,000, and the remaining solution comprises the material retained on said filter.

7. The antigen-containing extractant of claim 1 wherein the step of collecting comprises collecting the schistosomes on a sieve whose openings will not allow the worms to pass through and wherein the step of rinsing comprises slowly pouring or spraying the collected schistosomes from one to three times with a total volume of saline solution of from about five to about 30 ml per 100 worms.

8. The antigen-containing extractant of claim 7 wherein, in the step of extracting, the rinsed adult schistosomes are contacted with from about 1.0 ml to about 20 ml of saline extracting solution per gram of schistosomes.

9. A vaccine for immunizing mammals against infection by schistosomes comprising an antigenic material containing saline extract of live adult schistosomes obtained by the steps of:
    perfusing fresh, living adult schistosome worms from a host with a buffered saline solution;
    rinsing the perfused worms with from one to three low volume buffered saline solutions to remove only blood and non-worm blood solids, said rinsing not washing away any significant amount of antigenic material;
    contacting the rinsed worms with buffered saline extracting solution for a period of at least 30 minutes to obtain a saline extract antigenic material from said worms;
    centrifuging said saline extract for a period of time sufficient to remove substantially all of the worm bodies and other suspended solid particles from said saline extract, and recovering the supernatant which is at least substantially, completely free from suspended solids;
    eluting the supernatant through a gel partition chromatography column capable of separating high molecular weight components, wherein the eluant is buffered saline solution; and,
    recovering the eluted fractions containing the antigenic material.

10. The vaccine, according to claim 9, wherein before said centrifuging step, the low molecular weight components of said saline extract are removed by filtering the saline extract through an exclusion pore filter having a pore size which retains solution components having molecular weight greater than about 50,000, and recovering the saline extract retained on said filter for further processing.

11. The vaccine according to claim 10, wherein said exclusion pore filter has a pore size which retains solution components having molecular weight greater than about 100,000.

12. The vaccine according to claim 9 wherein the gel partition chromatography column is one which has an exclusion limit in the range of from about 100,000 to about 400,000, and the antigenic material is recovered in the first and second eluted fractions.

13. The vaccine according to claim 12 wherein the antigenic material recovered in the first eluted fraction comprises a first glycoprotein having a molecular weight in the range of from about 200,000 to less than about 400,000 and a second glycoprotein having a molecular weight in the range of from about 100,000 to about 200,000, wherein the glyco moiety of said glycoproteins is a mannose sugar moiety; and wherein the antigenic material recovered in the second eluted fraction comprises a protein having a molecular weight in the range of from about 40,000 to about 60,000, wherein said molecular weights are determined by gel filtration.

14. A method of extracting antigenic material from live adult schistosomes comprising the steps of:
   collecting fresh, living adult schistosomes from an infected host without destroying the schistosomes;
   rinsing the fresh, living adult schistosomes with saline solution to remove only blood and non-worm solids but without removing worm by-products;
   storing the collected adult schistosomes in a saline extracting solution for a period of at least about 30 minutes;
   removing the schistosomes from the saline extracting solution; and,
   collecting the remaining solution containing live worm-derived antigenic substance.

15. The method as set forth in claim 14 wherein the saline extracting solution consists essentially of a 0.15 M sodium chloride solution with a sodium phosphate buffer at pH 6.8.

16. The method as set forth in claim 15 wherein the step of removing comprises centrifuging the extracting solution, and collecting the supernatant as the remaining solution.

17. The method as set forth in claim 15 wherein the step of removing comprises filtering the extracting solution through a filter having an exclusion pore size which retains solution components having a molecular weight greater than about 50,000, and retaining the high molecular weight solution.

18. The method as set forth in claim 15 wherein the step of removing comprises filtering the extracting solution through a filter having an exclusion pore size which retains solution components having a molecular weight greater than about 100,000, and retaining the high molecular weight solution.

19. The method as set forth in claim 17 or 18 which further comprises centrifuging the remaining solution and collecting the supernatant as the remaining solution.

20. The method as set forth in claim 16 or 17 which further comprises purifying the remaining solution by passing the remaining solution through a gel partition chromatography column capable of separating high molecular weight components using buffered saline solution as the eluant, and recovering the first and second eluted fractions containing said antigenic material.

21. A method of immunizing a mammal against infection by schistosomes comprising administering to said mammal an effective dose of the antigen-containing vaccine of claim 9 to induce an immunological reaction.

22. The method of immunizing a mammal against infection by schistosomes as set forth in claim 21 further including the steps of periodically administering additional amounts of said vaccine as a booster to reinforce the immune reaction in the mammal.

23. The method according to claim 21 wherein said mammal is a human.

* * * * *

REEXAMINATION CERTIFICATE (461st)

United States Patent [19]

Messineo et al.

[11] B1 4,396,600

[45] Certificate Issued  Feb. 11, 1986

[54] ADULT SCHISTOSOME WORM-DERIVED ANTIGENIC SUBSTANCE AND METHOD OF OBTAINING SAME

[75] Inventors: Luigi Messineo, Broadview Heights, Ohio; Mauro Scarpin, Rio de Janeiro, Brazil

[73] Assignees: Gus Gallucci; Mike Gallucci, both of Akron, Ohio; Michael Gallucci, Jr., Broadview Heights, Ohio; Don Lower, Leesburg, Va. ; part interest to each

Reexamination Request:
  No. 90/000,687, Dec. 17, 1984

Reexamination Certificate for:
  Patent No.: 4,396,600
  Issued: Aug. 2, 1983
  Appl. No.: 217,575
  Filed: Dec. 18, 1980

[51] Int. Cl.⁴ .............................................. A61K 39/002
[52] U.S. Cl. .................................. 424/88; 260/112 R; 424/85; 424/93; 424/177; 436/515
[58] Field of Search ...................... 424/88, 85, 93, 177; 436/515

[56] References Cited
PUBLICATIONS

"The Presence of *Schistosoma mansoni* Antigens in Solutions used for Storing Adult Worms" (Revista do Instituto de Medicina Tropical de São Paulo, 21(6): pp. 293–296, nov–dez, 1979).

"Preliminary Studies with a *Schistosoma mansoni* Saline Extract Inducing Protection Against the Challenge Infection" (Revista do Instituto de Medicina Tropical de São Paulo, 22(4): pp. 164–172, jul–ago., 1980).

"Técnica de perfusão para colheita de *Schistosoma mansoni* em co-baias experimentalmente infestadas" (Revista Brasileira de Malariologia e Doenças Tropicais, vol. VIII, No. 4: 499–597, (1956).

*Primary Examiner*—Sam Rosen

[57]  ABSTRACT

An extract of adult Schistosome mansoni worms, obtained by incubation in 0.15M sodium chloride-sodium phosphate buffer (pH 6.8), contains protein, carbohydrates, and nucleic acid and/or by-products of the latter component and resolves into four major fractions by gel chromatography in G-100 and G-200 Sephadex columns. Immunodiffusion tests with rabbit anti-total extract serum reveal three precipitation lines corresponding to fractions I and II, and one with III or IV. Rabbits immunized with this total extract are found to be totally or partially (at least 77%) resistant to a challenge infection. The saline extract antigenic material is an effective vaccine for the treatment and immunization of schistosomiasis and other schistosome infections.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-23 are cancelled.

* * * * *